United States Patent [19]

Azria

[11] Patent Number: 4,988,512

[45] Date of Patent: Jan. 29, 1991

[54] NASAL PHARMACEUTICAL COMPOSITIONS

[75] Inventor: Moise Azria, Basel, Switzerland

[73] Assignee: Sandoz Ltd., Basel, Switzerland

[21] Appl. No.: 408,641

[22] Filed: Sep. 18, 1989

Related U.S. Application Data

[63] Continuation of Ser. No. 870,257, Jun. 3, 1986, abandoned.

[30] Foreign Application Priority Data

Jun. 4, 1983 [GB] United Kingdom ............... 8514090

[51] Int. Cl.$^5$ ..................... A61K 9/02; A61K 9/26; A61K 9/44
[52] U.S. Cl. ..................... 424/422; 424/425; 424/426; 424/434; 424/484; 424/485; 424/486; 424/488; 424/473; 514/808; 514/809
[58] Field of Search ................ 514/808, 869; 424/DIG. 15, 422, 425, 426, 434, 484, 485, 486, 488

[56] References Cited

U.S. PATENT DOCUMENTS

| | | | |
|---|---|---|---|
| 820,948 | 5/1906 | Baum | 604/288 |
| 3,234,091 | 2/1966 | Lang et al. | 424/DIG. 15 |
| 4,164,560 | 8/1979 | Folkman et al. | 424/486 |
| 4,294,829 | 10/1981 | Suzuki et al. | 514/174 |
| 4,371,516 | 2/1983 | Gregory et al. | 424/486 |
| 4,391,797 | 7/1983 | Folkman et al. | 424/486 |
| 4,452,775 | 6/1989 | Kent | 424/484 |
| 4,591,496 | 5/1986 | Cohen et al. | 424/467 |
| 4,613,500 | 9/1986 | Suzuki et al. | 424/477 |
| 4,652,441 | 3/1987 | Okada et al. | 424/DIG. 15 |
| 4,670,419 | 6/1987 | Uda et al. | 514/809 |

Primary Examiner—Shep K. Rose
Attorney, Agent, or Firm—Gerald D. Sharkin; Robert S. Honor; Walter F. Jewell

[57] ABSTRACT

Solid nasal inserts of calcitonin and other peptides have particularly interesting drug absorption profiles.

12 Claims, No Drawings

NASAL PHARMACEUTICAL COMPOSITIONS

This is a continuation of application Ser. No. 06/870,257, filed June 3, 1986 now abandoned.

The present invention relates to novel nasal inserts for the administration of pharmacologically active agents, especially proteins and peptides, in particular calcitonins.

The calcitonins comprise a class of pharmaceutically active, long chain polypeptides of varying, well documented pharmaceutical utility. The class includes not only the naturally occurring calcitonins, such as human, salmon, porcine and bovine calcitonin, but also various derivatives and analogues thereof, e.g. in which one or more of the amino acid residues or sequences naturally present is omitted, replaced, reversed or otherwise derivatised or in which the N- or C-terminal is modified. Various calcitonins, including e.g. human and salmon calcitonin and the eel calcitonin analogue Elcatonin are now commercially available and commonly employed, e.g. in the treatment of Paget's disease, hypercalcaemia and osteoporosis.

As is commonly the case with polypeptides however, provision of convenient and effective means of administering calcitonins has presented many difficulties. Being polypeptides, the calcitonins are susceptible to rapid degradation on enteral administration and only pass with difficulty into the body-fluids. For this reason parenteral administration has hitherto been the only route commonly available which permits effective treatment. Generally administration is by injection. Such means are always inconvenient and where administration is to be effected at regular intervals can cause considerable pain to the patient.

Recently, there has been an increasing interest in the possibility of administering pharmaceutically applicable peptides via the nasal route e.g. in the form of a nasal ointment or gel, or for greater accuracy of dosaging, in the form of a liquid nasal spray. The peptide insulin is a case in question and more recently proposals have been made for the nasal administration of calcitonins—see for example UK patent specification No. 2,127,689 A. While this latter proposal provides a viable and highly promising alternative to injection, yet further improved means of administration remain a major target.

We have now found that in such systems, e.g. powders, the absorption is affected by the mucociliary flow flushing way the active agent within a short-time. We have also now found that calcitonin peptides become degraded in the special physiological conditions found in the nose. These and other factors lower systemic absorption.

Various nasal insets have been contemplated for veterinary use in patent publications, but until now no satisfactory nasal insert has been used in humans. We have now found that a simple nasal insert system is well tolerated in humans and is sufficient in drug delivery.

In accordance with the present invention it has now surprisingly been found that by effecting nasal administration of pharmacologically active agents, e.g. pharmaceutically applicable peptides, for example calcitonins, employing a solid nasal insert as the peptide carrier system, greatly improved results may be obtained, e.g. in terms of patient compliance (e.g. facilitated self-application)/achievable accuracy of dosaging/bioavailability levels reached/duration of action, as compared with administration employing a liquid nasal spray as previously proposed.

We have moreover found certain nasal inserts are of particular interest for the administration of any systemically active pharmacologically active agent.

While the present invention is herein described primarily with reference to the administration of calcitonins, it is to be appreciated from what has been said above, that the invention is equally applicable to other pharmaceutically applicable peptide substances or other systemically active pharmacologically active agents. In its broadest aspect the invention is accordingly not to be understood as being in any way limited in relation to the pharmaceutically applicable peptide concerned.

By the term "pharmaceutically applicable peptide" is to be understood any peptide which is useful in the therapeutic treatment of the human or animal body.

In a first aspect the present invention provides a porous solid nasal insert comprising gelatine and/or hydroxypropylmethylcellulose carrying a systemically active pharmacologically active agent dispersed therein. In another aspect the present invention provides a solid nasal insert comprising a porous matrix comprising gelatine and/or hydroxypropylmethylcellulose having a lyophilisate of a systemically active pharmacologically active agent therein.

The nasal insert may be produced by any conventional method, e.g. by (a) producing a distribution of a systemically active pharmacologically active agent throughout a porous matrix comprising gelatine and/or hydroxypropylmethylcellulose, e.g. by lyophilising a liquid containing a polymer capable of forming a matrix, and a pharmacologically active agent or producing a distribution of a systemically active pharmacologically active agent throughout a porous matrix comprising gelatine and/or hydroxypropylmethylcellulose, or (b) distributing a calcitonin throughout a nasal insert, for example by soaking a sponge in an aqueous solution at e.g. room temperature and evaporation off the solvent. We have found that such inserts provide an especially advantageous absorption profile, providing good bioavailability over a long period with little drug burst when used for example with proteins and especially calcitonins. Especially conveniently the insert is formed under a vacuum.

In a further aspect the present invention provides a solid nasal insert carrying a calcitonin and capable of releasing said peptide to the surface of the nasal mucosa when inserted into the naris. Preferably the insert is porous, e.g. of substantially uniform porosity.

By the term "nasal insert" is to be understood, e.g. a device which is sized shaped and adapted for placement and retention into the naris: intended for insertion into the naris; or which is formed, shaped or otherwise adapted for insertion into and/or retention in the naris; or which is shaped to substantially conform to the internal surface of the naris; or which is provided with means to facilitate insertion into and/or retention in the naris; or which is provided with a dispenser device to facilitate insertion into the naris; or which is provided together with instructions to effect insertion into the naris. The insert may be retained in the naris, but flushed by the nasal mucous, and may be designed to release the active agent at the same place in the naris. Suitable nasal insert types include nasal plugs, tampons and the like. Conveniently the volume and porosity of the insert are chosen such that it is retained in the naris, but breathing is not significantly inhibited. Suitable dimensions are e.g. from about 0.1 to about 1 cm³, e.g. about 0.5 to about 0.8 cm³. The shape may be approximately e.g. a cylinder, a cone or a cube.

The agent may be carried on the insert, e.g. by adsorption onto the surface thereof, or in the insert, e.g. by absorption, or by any other convenient means, e.g. carried in combination with one or more nasally acceptable diluents or vehicles in the form of a coating, e.g. solid or semi-solid coating, upon the surface on the insert.

Alternatively, where the insert itself comprises a soluble or semi-soluble material, e.g. water-soluble polymers, or material otherwise degradable within the naris, for example a nasally acceptable protein-aceous material such as gelatin, the agent may be present in solid form in the form of lyophylisate dispersed within the insert, e.g. distributed throughout the matrix.

Preferably the agent is carried, e.g. retained, e.g. by absorption, in the insert and is suitably distributed throughout the volume of the insert.

Inserts in accordance with the invention are capable of releasing the peptide carried to the surface of the nasal mucosa. For this purpose they will preferably be so shaped or formed as to conform to the internal surface of the naris, e.g. so as to enable maximum contact between the surface of the insert and the nasal mucosa. Moreover, where the agent is retained in the insert, e.g. by absorption, its characteristics, e.g. the absorption characteristics of the material of which it is comprised, will suitably be such as to allow ready passage of the peptide to the surface of the insert following progressive uptake by the nasal mucosa from the insert surfaces.

Where agent is retained, e.g. by adsorption, in the insert, the insert may comprise any appropriate, e.g. nasally acceptable material, providing a porous matrix or reticulum in the interstices of which the peptide may be retained, e.g. absorbed. The material is conveniently elastic so it can be retained in the naris without discomfort. It may be for example, fibrous material, such as cotton wool or sponge material, such as natural or synthetic sponge.

If desired, the material may swell a little, e.g. increase in volume by about 50%, on administration.

The material from which the insert is fixed may be for example a water soluble polymer. Preferably the polymer is easily wettable by the nasal mucous. In the naris it may be biodegradable and, it may even dissolve slowly e.g. over up to one or more days. It may have to be removed after the dose of active agent has been administered. An example is lyophilised absorbable gelatine sponge. If desired the matrix may dissolve by the time or shortly after the dose of active agent has been administered. Examples include water-soluble acrylate polymers and cellulose derivatives such as cellulose, e.g. crystalline cellulose, hydroxypropyl-cellulose and especially hydroxypropylmethyl cellulose.

The characteristics of the matrix material used, e.g. viscosity or molecular weight should be chosen such that these resultant insert is easy to handle and store. Typical molecular weights for hydroxypropylmethyl A cellulose are from about 9,000 to 15,000 and a viscosity around 15 cp. for a 2% solution.

We have found as indicated above that an especially suitable material is a gelatin sponge material. Specifications have been laid down in the U.S. Pharmacopoea for absorbable gelatine sponges, e.g. for hemostatis in surgical procedures and such sponges are preferred. Such sponges may be produced e.g. by vigorously whipping an aqueous solution of pure gelatine to produce a foam, drying the foam under controlled conditions to give a sponge, cutting up the sponge and sterilizing the cut-up pieces. Suitable sizes are from about $5 \times 5 \times 5$ to about $10 \times 10 \times 10$ mm. The sponge is compressed by hand before use and is resorbed over a few hours. An especially suitable sponge material for use in the preparation of nasal inserts in accordance with the invention is the product SPONGOSTAN ® available from A/S Ferrosan, 5 Sydmarken, DK-2860 Soeborg, Denmark.

As indicated above the insert preferably has a porous structure. Conveniently the nasal mucous can wet the insert and the active agent may diffuse through the pores in the insert to the surface of the naris.

The pores of the insert may have a diameter of for example a few microns to about 100 microns. The pores of a lyophilised absorbable gelatin sponge may be for example from about 5 to 100 microns. The pore size may for example from about 5 to about 10 microns.

In sponge material the pores may be tortious. When the insert is produced under lyophilisation the pores may be approximately linear.

Preferably the insert contains a water-soluble sugar or like excipient to provide a stable structure to the insert. Examples of suitable sugars include lactose and mannitol. Preferably the weight ratio sugar to other material is from about 0.1 to 1 to about 10 to 1.

A preferred insert comprises a water-soluble polymer such as hydroxypropylmethyl cellulose and lactose. Under electron microscopy a lyophilised sample appears to comprise laminar sheets each having pores therein. The pores extend substantially throughout the sample.

Where the agent is retained in the insert, e.g. by adsorption, it will conveniently be carried in dilute form, e.g. in the form of a composition comprising the active agent together with a nasally acceptable fluid, e.g. liquid, diluent or vehicle therefor. Suitably such composition will comprise the agent in the form of a solution, suspension, dispersion or the like. Preferably such composition will comprise the agent in aqueous solution.

Suitable compositions, e.g. aqueous compositions, as aforesaid, include any of those known in the art for use as nasal spray formulations, for example, in the case of calcitonins, as described and claimed in the aforementioned UK patent specification No.2,127,689 A.

The insert is preferably formed under substantially microorganism-free or sterile conditions. In one preferred variante a solution of the active agent is lyophilisated. The insert may be preformed or formed during the lyophilisation process, e.g. from a solution of the insert material.

The lyophilisation may be effected under conventional conditions, preferably at low temperatures, e.g. ca. about $-100°$ C. to about $-10°$ C. Conventional pressure, e.g. ca. about 0.01 mm to about 0.2 mm mercury may be used.

Lyophilisation may produce an outer layer of very fine pores which may be sponge like. This outer layer may be about 10 to 100 microns thick. If desired its formation may be avoided by effecting the lyophilisation at very low temperatures. Alternatively it may be removed by rubbing.

Preferably such compositions will include a nasally acceptable absorption promoter, e.g. substance capable of promoting absorption via the nasal mucosae. Such promoters include nasally acceptable surface active agents or tensides. Such surface active agents include:

i. Bile acids and salts thereof, such as sodium taurocholate, sodium deoxycholate and sodium glycocholate ii. Cationic surfactants, such as long chain amine condensates with ethylene oxide and quaternary ammonium compounds, for example cetyl trimethyl ammonium bromide and dodecyl dimethyl ammonium bromide;

iii. Anionic surfactants such as alkylbenzenesulfonates; N-acyl-n-alkyltaurates, α-olefin sulfonates, sulfated linear primary alcohols and sulfated polyoxyethylene straight chain alcohols;

iv. Non-ionic surfactants, such as polyoxyethylenated alkylphenols, polyoxyethylene straight chain alcohols, long chain carboxylic acid esters including glycerol esters of natural fatty acids, propylene glycol, sorbitol and polyoxyethylene sorbitol esters, e.g. Polysorbate 80 ®.

v. Amphoteric surfactants, such as imidazoline carboxylates, sulfonates etc . . . ; and vi. Phospholipids, such as phospatidyl choline etc.

Especially preferred surfactants are polyoxyalkylene higher alcohol ethers, e.g. of the general formula I

$$RO\text{-}[(CH_2)_n\text{-}O]_x H \qquad (I)$$

wherein RO is the residue of a higher alcohol especially a higher alkanol or alkylphenol, such as lauryl or cetyl alcohol, or a sterol residue, especially a lanosterol, dihydrocholesterol or cholesterol residue, as well as mixtures of two or more such ethers. Preferred polyoxyalkylene ethers are polyoxyethylene and polyoxypropylene ethers (i.e. wherein n in the formula above is 2 or 3) in particular polyoxyethylene and polyoxypropylene lauryl, cetyl and cholesteryl ethers as well as mixtures of two or more such ethers.

The hydroxy group at the end alkylene unit of such ethers as aforesaid may be partially or completely acylated, by e.g. acyl residues of aliphatic carboxylic acids, such as acetic acid.

Preferred ethers have a hydrophilic-lipophilic balance (HLB group number) of from about 10 to about 20, especially from about 12 to about 16.

Especially suitable ethers are those wherein the average number of repeating units in the polyoxyalkylene moiety (x in the formula above) is from 4 to 75, suitably 8 to 30, more especially 16 to 26. The ethers may be obtained in accordance with known techniques. A wide variety of such products are commercially available and e.g. offered for sale e.g. by the company Amerchol under the trade-name Solulan ®, the companies KAO Soap, ICI and Atlas under the trade-names Emalex ®, Brij ® and Laureth ® from the company Croda under the trade-name Cetomacrogol ®.

Examples of suitable polyoxyalkylene ethers are as follows: (POE=polyoxyethylene ether; POP=polyoxypropylene ether; x=average No. of repeating units in the POP/POE moiety).

1. Cholesteryl ethers:
   1.1 Solulan ® C-24 - POE, x = 24.
2. Ethers of Lanolin alcohols:
   2.1 Solulan ® 16 - POE, x = 16.
   2.2 Solulan ® 25 - POE, x = 25.
   2.3 Solulan ® 75 - POE, x = 75.
   2.4 Solulan ® PB-10 - PPE, x = 10.
   2.5 Solulan ® 98 - POE, x = 10 - partially acetylated.
   2.6 Solulan ® 97 - POE, x = 9 - fully acetylated.

-continued

3. Lauryl ethers:
   3.1 Emalex ® 709 / Laureth ® 9 - POE, x = 9.
   3.2 Laureth ® 4 / Brij ® 30 - POE, x = 4.
   3.3 Laureth ® 23 / Brij ® 35 - POE, x = 23.
4. Cetyl ethers:
   4.1 Cetomacrogol ® - POE, x = 20 to 24.

Lanolin alcohols are also known as wool fat alcohols and are a mixture of cholesterol, dihydrocholesterol and lanosterol.

Preferred ethers are polyoxyethylene cholesteryl ethers, i.e. of the above formula I, wherein n=2 and RO is a cholesterol residue, especially such ethers wherein the number of repeating units in the polyoxyethylene moiety is from 16 to 26, most preferably about 24.

More preferably such ethers are substantially free from contaminents in particular from other polyoxyalkylene ethers. Most preferably they comprise at least 75%, more preferably at least 85%, and most preferably at least 90% by weight of pure polyoxyethylene cholesteryl ether.

When a surfactant, e.g. a polyoxyalkylene ether is employed, the amount present in the composition will vary depending on the particular surfactant chosen and the effect desired.

In general, however, the amount present will be of the order of from about 2.0 to about 200 (preferably to about 100, more preferably to about 20), suitably from about 5 to about 30 (preferably to about 15), and most preferably about 10 mg/ml.

If desired such compositions will also include a nasally acceptable sterilizing agent, benzalkonium chloride being especially preferred for this purpose.

In order to permit release from within the nasal insert to the nasal mucosae, active agent compositions employed should also possess a appropriate viscosity and for the purposes of nasal acceptability they should also possess an appropriate isotonicity. Preferably they have an osmotic pressure of from about 260 to about 380 mOsm/liter. The viscosity will suitably be less than $2 \times 10^{-3}$ Pa.S., e.g. from 1 to $2 \times 10^{-3}$ Pa.S.

The amount of agent carried in the inserts of the invention will of course depend on the particular agent chosen (e.g. if it is a calcitonin on its relative potency of activity), the conditions to be treated, the desired frequency of administration, the particular therapeutic effect required etc. The amounts required can be determined using conventional bioavailability comparisons of the nasal inserts of the invention and other e.g. known therapeutically effective forms containing the active agent. The comparisons may be effected in known or if desired in animal e.g. rabbit or monkey models. Where the agent is a calcitonin, e.g. salmon calcitonin, amounts present/insert will suitably be sufficient to permit administration of dosages of from ca.10 or ca. 50 to 400 MRC (or IU) units calcitonin at a rate of from ca. 1× daily to ca.3× weekly, whereby each treatment may, if desired, be effected by sequential administration of a series of e.g. 2 or 3 individual dosages. Inserts in accordance with the invention may accordingly each carry as little as from ca.3 or ca.5 or, more generally, from ca.10 or ca.25 to ca.400, preferably from ca.50 to ca.100 or ca.200 MRC units calcitonin. It is preferred that the dose of calcitonin peptides is released from the insert in up to 1, 2 or 3 hours. This leads to satisfactory drug plasma levels in the steady state (on repeated administration).

The insert may be wet. The insert may be packed into an applicator, e.g. a syringe. A predetermined volume of solution containing the active agent may then be applied and allowed to soak in. Preferably the insert is in dry form.

In order to prevent loss of agent from the inserts of the invention prior to use, i.e. prior to insertion into the naris, they will preferably be appropriately packaged, e.g. in a sealed, e.g. vacuum sealed, blister package, aluminium or plastics foil container or the like, or be presented in a appropriate sealed nasal applicator device. Most preferably the nasal inserts will be individually so packaged, or so packaged in pairs.

In addition to the foregoing the present invention also provides a method of administering a pharmaceutically active agent, e.g. a peptide, e.g. a calcitonin, to a subject requiring treatment therewith, which method comprises nasally administering a nasal insert as hereinbefore described, e.g. inserting an insert as hereinbefore described into the naris of said subject.

The following examples are illustrative of the present invention:

In the examples calcitonin=salmon calcitonin except where otherwise stated, hydroxymethylpropyl cellulose may be brand Methocel E5 from Dow USA or Pharmacoat 606. Further details are available from manufacturer's literature and/or H.P. Fiedler Lexicon der Hilfsstoffe, Editio Cantor Aulendorf, the contents of which are hereby incorporated by reference.

EXAMPLE 1

Preparation of Nasal Insert from Gelatine Sponge

A nasally acceptable, aqueous solution comprising salmon calcitonin, is prepared employing conventional formulation techniques and using the following ingredients in the indicated relative amounts.

| INGREDIENT | AMOUNT |
|---|---|
| a. Salmon calcitonin | 500 MRC (IU) |
| b. NaCl | 7.50 mg |
| c. Benzalkonium chloride | 0.10 mg |
| d. HCl (0.1 N) | to pH 3.7 |
| e. Water for injection | to an end volume of 1 ml. |

(a) Wet Sponge—1st Variante Nasal inserts are prepared from SPONGOSTAN ® by cutting into cubes each of 10×10×10 mm. 100 ul of the pre-prepared salmon calcitonin solution are brought into contact with each cube, together with a little 1% mannitol solution and allowed to diffuse evenly through the SPONGOSTAN, providing a nasal insert carrying 50 MRC (IU) salmon calcitonin.

Each insert may be packaged in a blister pack or aluminium or plastics foil to prevent loss of the solution carried therein, or compressed and placed in the delivery end of a syringe device having a delivery aperture sufficient to allow expression of the insert on actuation of the plunger, whereafter the delivery aperture may if desired be sealed by means of an appropriate closure device. Syringe devices as aforesaid allow ready application, i.e. by insertion of the delivery aperture into the lower naris followed by actuation of the plunger.

The nasal inserts may if desired be shaped to substantially conform to the internal surface of the naris, e.g. have a substantially cylindrical or tapering cylindrical form, conveniently with rounded ends.

The above procedure may be repeated employing salmon calcitonin solutions comprising e.g. 100, 250, 1000, 2000 or 4000 MRC (IU)/ml to provide inserts carrying e.g. 10, 25, 100, 200 or 400 MRC (IU) each.

(b) Wet Sponge—2nd Variante

The sponge of adsorbable gelatine sponge (Spongostan ®) sized about 10×10×10 mm is rolled into a cylinder (length 10 mm, diameter ca. 5 mm). It is fitted into the cylinder of a 1 ml plunger syringe the needle end of which has been cut off. 100 microlitres of a solution of calcitonin specified in Example 1 is syringe into the sponge (50 or 200 MRC Units of calcitonin). The 1 ml syringe is deep frozen to −35° C. and lyophilised for 2 hours at 0.01 mm Hg at −35° C.; and then for 66 hours at −15° C. The syringe is allowed to warm up in the vacuum to 15° C. The syringe is then packed into a polyethylene bag and sealed. The preparation is effected under sterile conditions.

The resultant insert is hard. Under electron microscopy it appears to have a high number of irregular pores. Pore diameter is from about 5 to about 100 microns.

The porosity is 0.7. Less than 10 per cent of the pores are sized less than 10 microns. More than 90 percent of the pores are sized less than 30 microns. Average pore size is around 20 microns with a 90 per cent probability.

EXAMPLE 2

Preparation of Nasal Insert from Hydroxypropylmethyl Cellulose 1.5 g of lactose (200 mesh) are dissolved in 30 g of pure water. The solution is heated to 79° C. 1 g of hydroxypropylmethyl cellulose are added to the solution. The solution was cooled to room temperature. The pH is adjusted to pH 3.7 with 0.1N HCl. 15 grams pure water are used to dissolve 0.02346 g calcitonin. The pH is adjusted to pH 3.7 with 0.1N HCl. The solutions are mixed and water added to 50 ml. The solution is filtered through 0.2 micron holes, and pipetted in 0.1 ml lots into depressions (5 mm) in a aluminium plate. The plate is cooled to −48° C. and lyophilisated at −48° C. for 2 hours. Then lyophilisation continues for 16 hours with raising of the temperature from −48° C. to +23° C. The resultant lyophilisate blocks are carefully removed from the place and inserted into a 1 ml syringe fitted with a plunger the needle end of which has been cut off about 3 mm from the end. Each block weighs about 4.95 mg and can have about 200 MRC. Units calcitonin 0.04688 mg, 3 mg lactose and 2 mg hydroxypropylmethyl cellulose.

The resultant insert is soft and easily disolvable in water. It is a uniform lyophilisate sized about 5 mm in diameter and about 6 to 7 mm in length. Under the electron microscopy it appears as a laminar ordered sheet system with long parallel pore channels of diameter about 5 to 10 microns. The edge of the lyophilisate is a layer of about 50 microns having a fine, foam-like, porous structure.

The porosity is 0.39. 80 per cent of the pores are between 5 and 17 microns.

EXAMPLE 3

Comparative Bioavailability Study: Application of Salmon Calcitonin Carried on a Nasal Insert vs. Application Employing a Nasal Spray

Trial A

The trial is carried out employing groups of 6 rhesus monkeys each weighing ca. 7.5 to 10 kg.

Test animals receive:

(1) Two nasal inserts (1 per naris) as described in example 1. Wet sponge Variante 1 each carrying 50 MRC (IU) salmon calcitonin, thus giving a total dosage of 100 MRC (IU); or (2) A liquid composition formulated as described in example 1. Wet sponge Variante 1 and comprising 500 MRC (IU) salmon calcitonin, delivered in the form of a nasal spray from a nasal spray applicator device delivering 100 ul/spray actuation, employing 2 actuations/animal (1/naris), thus again giving a total dosage of 100 MRC (IU); or (3) Two placebo nasal inserts (1/naris) prepared as described in example 1 but with omission of salmon calcitonin.

2.5 ml blood samples are collected at 0, 0.8, 0.16, 0.25, 1, 1.5, 2, 3, 4 and 6 hours on Li heparinate and the plasma frozen and later assayed for salmon calcitonin employing a standard RIA assay kit.

Comparison of results for animals receiving treatment as under (1) and (2) with animals in group (3) receiving placebo indicate that:

The AUC and relative bioavailability is greater in group (1) as compared with group (2): AUC=0.533 m IU.ml-h.

Relative bioavailability in group (1) vs. (2)=276.30% (+176.30%).

Increased salmon calcitonin plasma levels in group (1) as compared with group (2): Cp max=0.352 mIU/ml vs. 0.055 mIU/ml after t max=0.08 h.

Trial B

The trial is carried out using groups of 6 rabbits (New Zealand, ca 690 g). A small Spongostan insert of 5 mm×5 mm×5 mm was made up in analogous manner to that described in Example 1, Wet sponge Variante 1, using 9 microliters of solution containing 550 IU of Salmon Calcitonin. The insert was administered to one nostril in a group. 9 microliters of salmon calcitonin solution was administered to one nostril in another group. The Plasma calcium concentration was determined using the ion selective electrode method.

|  | Composition of the Invention | Reference |
| --- | --- | --- |
| Max effect in lowering calcium levels | −19.04% | −14.59% |
| T max | 3 hours | 1.5 hours |
| AUC (0–5 hrs) (0%/hr) | −71.78% | −23.40% |
| Relative Bioavailability | 307% | 100% |

Excellent tolerability was observed with the compositions of the invention. Moreover they had a significant duration of action. After 5 hours −12% less calcium levels were observed with compositions of the invention. With the reference composition after 3 hours no significant drop in calcium levels was observed.

Trial C

A clinical trial may be effected over a series of six treatment days in six subjects. A solid insert containing 200 MRC calcitonin is inserted into each nostril. Blood samples are obtained 5, 10, 15 and 30 minutes after administration and 1, 1.5, 2, 3, 4, 5, 6 and 8 hours after administration. The levels of salmon calcitonin in the blood and the calcium levels in the blood are determined by conventional methods.

Bioavailability is assessed using the following parameters:

Area under the curve
Maximum plasma concentration
Time of maximum plasma concentration
Elimination half life Porosity of the inserts of the invention is measured by the mercury intrusion method which also gives an estimate of the pore size distribution.

Conveniently, the porosity is from about 0.3 to 0.8, e.g. 0.3 to 0.5 or 0.6 to 0.8. Conveniently, at least 50 per cent (e.g. up to 80 per cent) of the pores are around from 5 to 25 microns.

What we claim is:

1. A porous solid nasal insert shaped to substantially conform to the internal surface of the naris comprising a porous gelatine sponge carrying a systemically active pharmacologically active agent dispersed therein wherein the active agent is calcitonin.

2. A solid nasal insert shaped to substantially conform to the internal surface of the naris comprising a porous matrix comprising a porous gelatine sponge having a lyophilisate of systemically active pharmacologically active agent therein wherein the active agent is a calcitonin.

3. A solid nasal insert shaped to substantially conform to the internal surface of the naris carrying a calcitonin peptide and capable of releasing said peptide to the surface of the nasal mucosa when inserted into the naris wherein the insert is a porous gelatine sponge.

4. An insert according to claim 1 comprising a porous matrix or reticulum, having calcitonin retained prior to insertion into the naris in the interstices thereof.

5. An insert according to claim 4 wherein the peptide is salmon calcitonin.

6. A method of administering a pharmacologically active agent to a subject requiring treatment therewith, which method comprises nasally administering an insert as claimed in claim 1.

7. Improved intranasal use of a nasal insert to administer a pharmacologically active calcitonin using an insert of claim 1 which comprises intranasally applying a preformed sponge which has been filled with an aqueous solution of the calcitonin.

8. Improved intranasal use of a pharmaceutical composition to administer a calcitonin using a porous insert of claim 3 which comprises intranasally applying a preformed sponge which has been filled with an aqueous solution of a calcitonin.

9. Improved intranasal use of a nasal insert to administer a pharmacologically acting calcitonin agent using an insert of claim 1 which comprises intranasally applying a preformed sponge which has been filled with an aqueous solution of the calcitonin and then lyophilising the resulting sponge.

10. Improved intranasal use of a pharmaceutical composition to administer a calcitonin using a porous insert of claim 3 which comprises intranasally applying a preformed sponge which has been filled with an aqueous solution of a calcitonin and then lyophilising the resulting sponge.

11. The porous nasal insert of claims 1, 2 or 3 having a surface active agent comprising bile acids and salts thereof.

12. The porous nasal insert of claim 11 where in the bile acid is selected from the group consisting of sodium taurocholate, sodium deoxycholate, and sodium glycoholate.

* * * * *